(12) United States Patent
Madangopal et al.

(10) Patent No.: US 10,480,091 B2
(45) Date of Patent: *Nov. 19, 2019

(54) SENSORS AND METHODS OF MANUFACTURE THEREOF

(71) Applicant: Purdue Research Foundation, West Lafayette, IN (US)

(72) Inventors: Rajtarun Madangopal, West Lafayette, IN (US); Jenna L. Rickus, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/373,154

(22) Filed: Apr. 2, 2019

(65) Prior Publication Data

US 2019/0226111 A1    Jul. 25, 2019

Related U.S. Application Data

(63) Continuation of application No. 14/254,475, filed on Apr. 16, 2014, now Pat. No. 10,287,699.

(60) Provisional application No. 61/812,706, filed on Apr. 16, 2013.

(51) Int. Cl.
| | |
|---|---|
| *G01N 27/327* | (2006.01) |
| *C25D 7/00* | (2006.01) |
| *C09D 5/24* | (2006.01) |
| *C25D 5/48* | (2006.01) |
| *C25D 3/56* | (2006.01) |

(52) U.S. Cl.
CPC .............. *C25D 7/00* (2013.01); *C09D 5/24* (2013.01); *C25D 5/48* (2013.01); *G01N 27/3271* (2013.01); *C25D 3/567* (2013.01); *G01N 27/3276* (2013.01)

(58) Field of Classification Search
CPC . C25D 7/00; C25D 5/48; C25D 3/567; C09D 5/24; G01N 27/327–3278
See application file for complete search history.

(56) References Cited

FOREIGN PATENT DOCUMENTS

| WO | WO-8800342 A1 * | 1/1988 | ............. G01N 27/49 |
| WO | WO-2010076717 A1 * | 7/2010 | ........... G01N 27/333 |

OTHER PUBLICATIONS

A. F. Revzin, etal., Glucose,lactate, and pyruvate biosensor arrays based on redox polymer/oxidoreductase nanocomposite thin-films deposited on photolithographically patterned gold microelectrodes, Sensors and Actuators B, vol. 81, pp. 359-368 (2002) (Year: 2002).*

(Continued)

*Primary Examiner* — Maris R Kessel
(74) *Attorney, Agent, or Firm* — Brown Rudnick LLP; Adam M. Schoen (57) ABSTRACT

The invention generally relates to sensors, methods of manufacture thereof, methods of use thereof for sensing analytes, such as small molecules and biomolecules, and methods of immobilization. In certain embodiments, the invention provides a multi-analyte sensor. The multi-analyte sensor includes a plurality of sensing electrodes. Each sensing electrode is functionalized with a different molecule (e.g., biomolecule), at least two of the sensing electrodes are spaced apart prior to and after functionalization by 100 μm or less, and there is no cross-talk between the plurality of sensing electrodes.

20 Claims, 10 Drawing Sheets

(56) References Cited

OTHER PUBLICATIONS

A. L. Simonian, et alCharacterization of oxidoreductase-redox polymer electrostatic film assembly on gold by surface plasmon resonance spectroscopy and Fourier transform infrared-external reflection spectroscopy, Analytics Chimica Acta, vol. 466, pp. 201-212 (2002) (Year: 2002).*
Yon Hin et al., Multi-analyte Microelectronic Biosensors, Sensors and Actuators, B1, pp. 550-554 (1990) (Year: 1990).*
Vidal et al., In situ preparation of overoxidized PPyroPPD bilayer biosensors for the determination of glucose and cholesterol in serum, Sensors and Actuators, B 57, pp. 219-226 (1999) (Year: 1990).*
Yan et al., Immobilizing Enzymes onto Electrode Arrays by Hydrogel Photolithography to Fabricate Multi-Analyte Electrochemical Biosensors, Applied Materials & Interfaces, vol. 2, No. 3. pp. 748-755 (2010).*

* cited by examiner

SENSORS AND METHODS OF MANUFACTURE THEREOF

RELATED APPLICATION

This application is a continuation of U.S. nonprovisional application Ser. No. 14/254,475, filed Apr. 16, 2014, which is claims the benefit of and priority to U.S. provisional application Ser. No. 61/812,706, filed Apr. 16, 2013, the content of which is incorporated by reference herein its entirety.

GOVERNMENT SUPPORT

This invention was made with government support under RR025761 awarded by the National Institutes of Health. The government has certain rights in the invention.

FIELD OF THE INVENTION

The invention generally relates to sensors, methods of manufacture thereof, methods of use thereof for sensing analytes, such as small molecules and biomolecules, and methods of immobilization.

BACKGROUND

Fabrication of electrodes with high spatial resolution and patterning are now mainstream methods in microfabrication and biosensing. The spatial patterning of different biorecognition molecules (e.g. antibodies, enzymes, aptamers) has not kept pace in practice. By far, the most common methods of biomolecule functionalization of electrodes for routine fabrication of biosensors for physiology are dip-coating, drop-coating, or spin-coating, none of which can be used to functionalize two nearby electrodes (micron scale spacing) with two different biomolecules for multi-analyte sensing.

Top-down approaches such as dip pen lithography or contact printing can be used, but these are hindered by speed, requirement for highly specialized equipment or the need for master templates. Alignment between the electrode and the depositing pen or mask is a primary challenge that becomes more difficult as spatial features decrease in size. Bottom up approaches typically rely on the chemical selectivity of the coupling chemistry to achieve spatially controlled deposition of specific biomolecules, limiting the number of unique sensors that can be created in a small space. In addition, specific coupling chemistries may be limited to the type of electrode material (e.g. thiol linkages to gold) or biomolecule of interest. In order to decorate nearby microelectrodes with different recognition biomolecules, a method needs to be developed to selectively control molecular deposition to each electrode.

SUMMARY

The invention provides methods of manufacturing sensors in which nearby electrodes (e.g., electrodes separated on the micro scale) can be selectively decorated with molecules of interest, such as biomolecules, allowing for the controlled and selective immobilization of the molecules on the nearby electrodes. With methods of the invention, pre-selected electrode sites are decorated with molecules of interest without any measurable deposition at a non-addressed nearby electrode site. Aspects of the invention are accomplished by using the electrode itself to direct functionalization on specific electrodes by electrochemical deposition.

The methods of the invention involve controlling the potential bias on proximate electrodes. A plurality of electrode tips are exposed to a medium containing a molecule (e.g., a biomolecule), and only the electrode that is biased during exposure to the medium is decorated with the molecule. The sensitivity of each individual electrode can be tuned by controlling the net charge input during deposition, and importantly there is no cross talk between the different electrodes. In that manner, the invention provides sensor manufacturing methods that are simple, fast, tunable, and do not require highly specialized equipment. Further, active use of the conductive substrate in the immobilization allows the implementation of this method on various shapes, sizes and 3D orientations of conductive surfaces in a high throughput fashion.

In certain aspects, the invention provides methods for functionalizing a plurality of electrodes with different molecules, such as biomolecules. Methods of the invention involve providing first and second electrodes, and introducing the first and second electrodes to a first medium including at least a first molecule and in some embodiments, more than one type of molecule. The first electrode is electrically biased and the second electrode is held at 0 mV or slightly negative, while the first and second electrodes are both in the first medium, which results in only the first electrode being functionalized with at least the first molecule. The first and second electrodes are then introduced to a second medium including at least a second molecule. Only the second electrode is electrically biased and the first electrode is held at 0 mV or slightly negative, while the first and second electrodes are both in the second medium, which results in only the second electrode being functionalized with at least the second molecule.

In certain embodiments, after the first electrode is functionalized with the first molecule (e.g., biomolecule), it is functionalized with a second molecule (e.g., biomolecule) by electrical biasing in a second medium including the second molecule. Various combinations of electroactive monomer and molecule (e.g., biomolecule) can be used in each consecutive layer to achieve specific stacking for the intended application. In certain embodiments, a plurality of molecules are immobilized per layer. For example two enzymes that work together to convert an analyte to a product can be placed in a single medium so that both enzymes are part of a layer that is formed on a sensing electrode. In another example, a blend of antibodies is immobilized in a single layer, which may be useful to detect a 'fingerprint' of a disease state.

In certain embodiments, prior to introducing the first and second electrodes to the first medium, the method further involves forming an electrically conductive layer (e.g., a platinum black layer) on the first and second electrodes. In certain embodiments, prior to introducing the first and second electrodes to the first medium, the method may further involve physically coupling the first and second electrodes to each other such that the first and second electrodes are spaced apart by, for example, 100 μm or less prior to and after functionalization. Such physical coupling could be expanded to multi-wire bundles or chip based electrode arrays for high throughput multi-molecule immobilization.

The first medium includes an electrically conductive material, such as an electrically conductive polymer. Electrically biasing the first electrode may involve applying at least one cycle of cyclical voltage in the range between 0 mV to 1800 mV to only the first electrode. The application of voltage to the first electrode initiates a polymerization reaction at only the first electrode that results in production of a layer of the electrically conductive material including the first molecule on only the first electrode. The second electrode is held at a voltage between 0 mV and negative 100 mV (−100 mV) to exclude any depositing layer.

The second medium will also include an electrically conductive material, which may be the same or different from the electrically conductive material of the first medium. In certain embodiments, the same electrically conductive material, e.g., the same electrically conductive polymer, is used in the first and second medium. Electrically biasing the second electrode may involve applying at least one cycle of cyclical voltage in the range between 0 mV to 1800 mV to only the second electrode. The application of voltage to the second electrode initiates a polymerization reaction at only the second electrode that results in production of a layer of the electrically conductive material including the second molecule on only the second electrode. The first electrode is held at a voltage between 0 mV and −100 mV to exclude any depositing layer.

Another aspect of the invention provides a multi-analyte sensor. The multi-analyte sensor includes a control unit and a plurality of sensing electrodes. Each sensing electrode is functionalized with a different molecule, at least two of the sensing electrodes are spaced apart prior to and after functionalization by 100 μm or less, and there is no cross-talk between the plurality of sensing electrodes. The sensor may be configured to operate in vitro or in vivo.

Numerous different techniques may be used to functionalize the electrodes with the molecules. In certain embodiments directed to generating a biosensing electrode and methods of use thereof, each sensing electrode includes a first layer including an electrically conductive material, a second layer including a first electrically conductive biocompatible material, and a third layer including a second electrically conductive biocompatible material. In certain embodiments, conductivity of the second electrically conductive biocompatible material is pH dependent. The biomolecule is present in the second and third layers of each sensing electrode respectively. Numerous different electrically conductive materials exist that may be used in the layers, e.g., polymers, semiconductors, metals, etc. In certain embodiments, an electrically conductive polymer is used in the second and third layers. In certain embodiments, the same electrically conductive polymer is used in the second and third layers. In other embodiments, a different electrically conductive polymer is used in the second and third layers. In an exemplary embodiments, the first layer is platinum black, the first electrically conductive biocompatible material is poly(3,4-ethylenedioxythiophene), and the second electrically conductive biocompatible material is poly(o-aminophenol). In other embodiments, the sensing electrode is generated using only the second and third layers previously described, and excluding the first layer of electrically conductive material. In further embodiments, the sensing electrode includes a layer including a conductive polymer and a first biomolecule, and a second layer including the conductive polymer and a second biomolecule different from the first biomolecule. This second biomolecule may be used to prevent non-specific interactions with the first biomolecule.

Another aspect of the technique allows for controlling the concentration of molecule coupled to the conductive polymer layer by controlling a number of voltage cycles. The more cycles applied will result in an increase in molecule deposition on the sensing electrode. That feature allows a plurality of sensing electrodes to have a gradient of molecule deposition concentration on the sensor (e.g., a gradient of biomolecule deposition concentration). That allows, for example, the detection of rare or small concentrations of a molecule of interest in a sensing environment. It can also allow the mapping of concentration gradients of molecules of interest in 3D space.

There are numerous different system configurations for the multi-analyte sensors of the invention. In one configuration the system includes, a control unit, which may optionally include a multi-potentiostat, a reference electrode and a counter electrode, and a first sensing electrode. In other configurations, the multi-analyte sensor comprises a second sensing electrode.

Another aspect of the invention provides a sensor. The sensor includes a control unit and at least one sensing electrode coupled to the control unit. At least a portion of the sensing electrode includes a first layer including an electrically conductive material, a second layer including a first electrically conductive biocompatible material and a molecule (such as a biomolecule), and a third layer comprising a second electrically conductive biocompatible material and the molecule. In certain embodiments, conductivity of the second electrically conductive biocompatible material is pH dependent. In certain embodiments, the first layer is platinum black, the first electrically conductive biocompatible material is poly(3,4-ethylenedioxythiophene), and the second electrically conductive biocompatible material is poly(o-aminophenol). The sensor may be configured to operate in vitro or in vivo.

In certain embodiments, the sensor includes a second sensing electrode. The second sensing electrode includes a first layer comprising an electrically conductive material, a second layer including a first electrically conductive biocompatible material and a second molecule (e.g., biomolecule), and a third layer including a second electrically conductive biocompatible material and the second molecule. In certain embodiments, conductivity of the second electrically conductive biocompatible material is pH dependent. In certain embodiments, the sensing electrodes are spaced apart by 100 μm or less.

The methods of the invention can be used to couple any molecules (e.g., biomolecules) known in the art to electrodes, and any molecule known in the art can be used with any of the sensors of the invention. Exemplary molecules are biomolecules, and exemplary biomolecules include enzymes, proteins, poly-peptides nucleic acids (e.g., DNA or RNA), antibodies, or aptamers.

In one embodiment the sensor detects electrons produced during controlled reaction to identify and quantify the presence of a molecule of interest. In another embodiment, the sensing electrode includes fluorescent molecules that are detected optically when there is a binding event between a molecule of interest and the biomolecule incorporated in a layer of the sensing electrode.

BRIEF DESCRIPTION OF THE DRAWINGS

FIG. 2 panels A-B depict an electrode setup & electrodeposition sequence. A custom three-electrode setup (panel A) allows small volume electrodeposition of enzyme doped polymer layers to reduce biomolecule waste. Panel B outlines the electrodeposition sequence for fabrication of a dual analyte stereotrode for simultaneous glucose and lactate sensing. Sequential deposition of three individual sensing layers each (1-3 for glucose sensor on tip 1; 1,4-5 for lactate sensor on tip 2) enables high resolution multi-analyte sensing.

FIGS. 7A-C are graphs showing that enzyme doping via PEDOT electrodeposition offers tunable sensitivity. Use of DMSO and elevated electrodeposition voltages causes the growth of a PEDOT film with reduced conductivity as shown by the progressively reduced charge injection and decreasing area under the cyclic voltammograms (7A). However higher potentials enable tuning of sensor sensitivity with varying numbers of polymer film growth cycles (7B). Tuning curve is linear with extent of film growth (7C).

FIG. 9 is a graph showing that stereo-electrode sensors showed no crosstalk. Shown are simultaneously recorded responses of the two microelectrode sensors to three additions each of lactate and glucose at a biasing potential of 0.5 V. Both sensors respond to changes in concentration of their respective analytes and show negligible response to additions of the other analyte. Rapid stirring was used to minimize diffusion related effects and demonstrate the absence of crosstalk. Signal spikes are a result of stirring noise and can be minimized in future designs by using an additional undoped concentric reference electrode.

DETAILED DESCRIPTION

In certain aspects, the invention provides molecule (e.g., biomolecule) deposition methods that can be addressed to specific, pre-selected electrode sites without any measurable deposition at a non-addressed nearby electrode site. The methods of the invention are simple, fast, tunable, and do not require highly specialized equipment.

Figure 1:
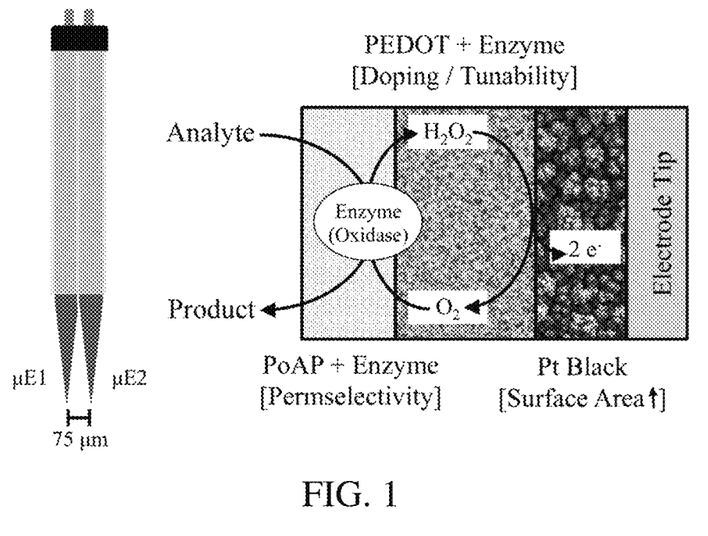
FIG. 1 depicts a multi-layer biosensor functionalization scheme. The three-layer scheme (Layer 1: Platinum Black, Layer 2: PEDOT+Enzyme, Layer 3: PoAP+Enzyme) allows for controlled functionalization of electrode tips with desired enzymes for multi-analyte sensing with enhanced sensitivity and selectivity.

FIG. 1 shows an embodiment of an exemplary sensor produced by methods of the invention. As shown in FIG. 1, a sensor of the invention generally includes at least one sensing electrode coupled to a control unit. The control unit is not required to be electrically coupled to sensors of the invention. For example, in certain embodiments, a deposited biomolecular layer is used as a biodetection/biorecognition region using other techniques such as optical (fluorescence/FRET), mass spec, NMR, surface plasmon resonance etc. In those embodiments, the control unit is an entity that is used for detection at some later stage and may or may not be electrically coupled to the substrate.

A sensor may include more than one sensing electrode, optionally electrically coupled to a control unit, generating a multi-analyte sensor. The sensing electrodes can have any orientation with respect to each other. As shown in FIG. 1, the sensing electrodes align with each other in the same direction, although this is not required. For example, sensing electrodes can be orthogonal to each other. In certain embodiments, the sensor is a chip, such as a microchip, and the sensing electrodes are incorporated into the microchip. In an exemplary embodiments, the microchip includes a substrate and the sensing electrodes are wires having functionalized portions, such as functionalized tips. The wires are incorporated into the substrate in a manner in which the functionalized portion of each sensing electrode is able to interact with analytes in a sample.

The sensor may be in any configurable shape, for example, a cube, a sphere, or a polygon. The sensing electrodes may be coupled to a non-conducting material, such as plastic, that may be rigid or flexible. Multiple sensors can be coupled together to form a sensor array.

The control unit includes a reference electrode and a potentiostat. In other embodiments the control unit includes a reference electrode, a counter electrode, and a potentiostat. The potentiostat may be a bi-potentiostat or a multi-potentiostat.

FIG. 1 shows first and second electrodes that have been differently functionalized using methods of the invention. The electrodes are shown 75 µm apart, which is only exemplary. Any distance apart of about 100 µm or less can be achieved using methods of the invention. For example, the electrodes can be 95 µm apart or less, 90 µm apart or less, 85 µm apart or less, 80 µm apart or less, 75 µm apart or less, 70 µm apart or less, 65 µm apart or less, 60 µm apart or less, 55 µm apart or less, 50 µm apart or less, 45 µm apart or less, 40 µm apart or less, 35 µm apart or less, 30 µm apart or less, 25 µm apart or less, 20 µm apart or less, etc. As explained in more detail below, the function of the electrode itself directs functionalization on specific electrodes by electrochemical deposition of a molecule (e.g., a biomolecule) within a medium including an electroactive biocompatible material (i.e., electrically conductive material). FIG. 1 and aspects of the application discuss a specific embodiment of the invention, referring to specific biomolecules, e.g., enzymes, and specific electroactive biocompatible material, e.g., electroactive biocompatible polymers. The skilled artisan will recognize that FIG. 1 and certain aspects of the application herein are exemplary, and not limiting of the scope of the invention. For example, numerous different electroactive biocompatible materials can be used in the methods and sensors described herein, and the invention is not limited to those materials specifically exemplified below. Similarly, the methods of the invention can be used to couple any molecules (inclusive of molecules that are not biomolecules) known in the art to electrodes, and any molecule known in the art can be used with any of the sensors of the invention. Particularly, the invention is not limited to those biomolecules specifically exemplified below.

Exemplary electroactive biocompatible materials for use with methods and sensors of the invention generally include metals, semi-conductors and polymers. Exemplary electroactive biocompatible materials are poly-thiophenes, poly-acetylenes, poly-pyrroles, poly-anilines, poly-indoles, poly-phenylenediamines, poly-phenols, and various derivatized versions of these polymeric classes.

Exemplary molecules are biomolecules and non-biomolecules. In certain embodiments, the molecule is a biomolecule. Exemplary biomolecules for use with methods and sensors of the invention generally include enzymes, proteins, poly-peptides, nucleic acids (e.g., DNA and RNA), nucleotides, antibodies, aptamers, small organic molecules, lipids, mono- or poly-saccharides, glycolipids, sterols, glycerolipids, vitamins, hormones, neurotransmitters, or metabolites. Other biomolecules are known in the art and are described, for example in Mishra ("Biomolecules", Discovery Publishing House, Jan. 1, 2003), the content of which is incorporated by reference herein in its entirety.

Referring back to FIG. 1, which illustrates a specific embodiment of the invention, the function of the electrode itself directs functionalization on specific electrodes by electrochemical deposition of protein within a polymer matrix of two electroactive polymers, namely poly(3,4-ethylenedioxythiophene) [PEDOT] and poly(o-aminophenol) [PoAP]. PEDOT was chosen as its formation from EDOT monomer can be controlled by electrode potential. PEDOT is also compatible with proteins, and has been recently used in the fabrication of biosensors with improved conductivity and good thermal and chemical stability. PoAP, the second polymer layer used in this functionalization scheme, affords improved selectivity to the analyte of interest owing to its unique pH dependent conductivity. While several recent studies have shown that electroactive polymers can be used to enhance sensitivity, selectivity and linear range of enzyme-based biosensors, most deposition schemes reported to date rely on passive enzyme adsorption at the electrode surface and therefore lack tunability. Further, these schemes are typically implemented on relatively large electroactive surfaces and the miniaturization and multiplexing of such sensors for multi-analyte detection is still fairly unexplored.

Methods of the invention demonstrate that by proper selection of monomer materials and deposition parameters, the in situ growth of polymer materials can be coupled with electro-aided enzyme adsorption to achieve enzyme-based amperometric sensors with tunable sensitivity and selectivity. Further, the same functionalization scheme can be extended to achieve simple spatially addressable doping of multiple enzymes of interest by controlling the potential on proximate electrodes to 0 mV or slightly negative. A fused stereo-microelectrode was designed in which two 1-2 μm diameter microelectrode tips are separated by about 75 μm, which is an only exemplary distance as discussed above (FIG. 1 and FIG. 3 panel A).

Both microelectrode tips were exposed to two different PEDOT/enzyme solutions, but only the electrode that is biased during exposure to glucose oxidase became a glucose sensor and only the electrode that was biased during exposure to lactate oxidase became a lactate sensor. The sensitivity of each individual sensor can be tuned by controlling the net charge input during deposition, and most importantly there was no cross talk between the glucose and lactate detection of the two nearby sensors. This system demonstrates the ability to address specific electrode sites simply by controlling potential bias thus creating an easy and tunable method for creating multi-analyte micro-sensors within small sensing areas. In addition, the method is generic to both the sensing element material and the recognition biomolecule and can thereby enable novel patterns of high-density, multi-analyte biosensor arrays. This is the first demonstration of the use of electroactive polymer nanocomposites for miniaturized, multiplexed, tunable biomolecule-based (e.g., enzyme-based) biosensors.

Figure 3:
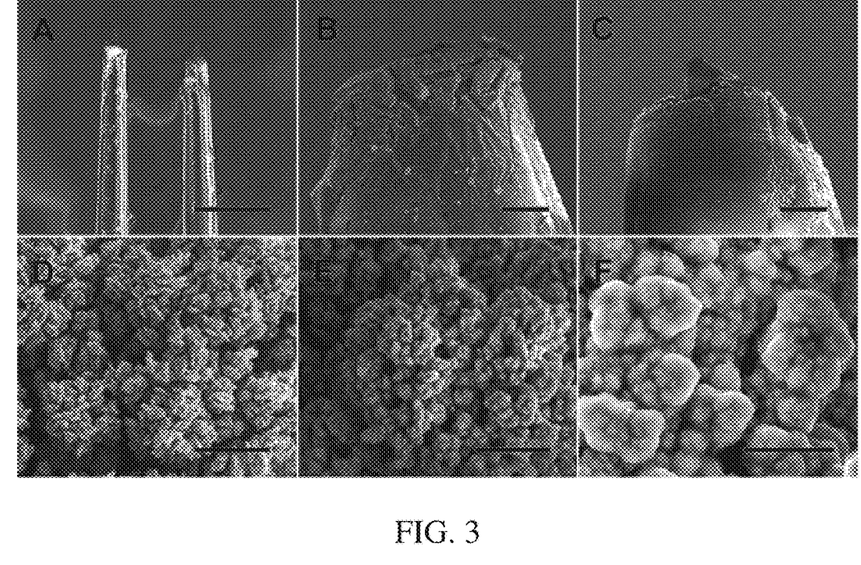
FIG. 3 panels A-F are scanning electro micrographs (obtained using a FEI NOVA nanoSEM FESEM under high vacuum with a power setting of 3-5 kV and 5-50 kX) of microelectrode at different stages of functionalization show highly localized deposition of individual sensing layers. (Panel A) Bare stereo-electrode with 75 µm tip spacing. (Panel B) Microelectrode tip before and (Panel C) after cleaning in $H_2SO_4$. Morphology of sensor tip after controlled electrodeposition of Platinum Black (Panel D), PEDOT film doped with enzyme (Panel E) and PoAP film doped with enzyme (Panel F). Scale bars in panels A, B-C and D-F are 50 µm, 5 µm and 1 µm respectively.

Single micro-wire electrodes were chosen as sensor substrates based on prior experience in the use of these materials for the development of micro-scale amperometric biosensors. FESEMs of the commercial single and stereo microelectrodes displayed irregular tip profiles (FIG. 3, panel B) that were successfully cleaned and exposed (FIG. 3 panel C) using several potential cycles in sulfuric acid. Electrodeposition of platinum black onto the exposed tip using a pulsed current scheme resulted in an intricate cauliflower like morphology (FIG. 3, panel D). Subsequent PEDOT and PoAP electrodeposition via potential cycling produced additional thin film like coatings that were highly localized on the initial growth of nanostructure platinum (FIG. 3, panels E-F).

Figure 4:
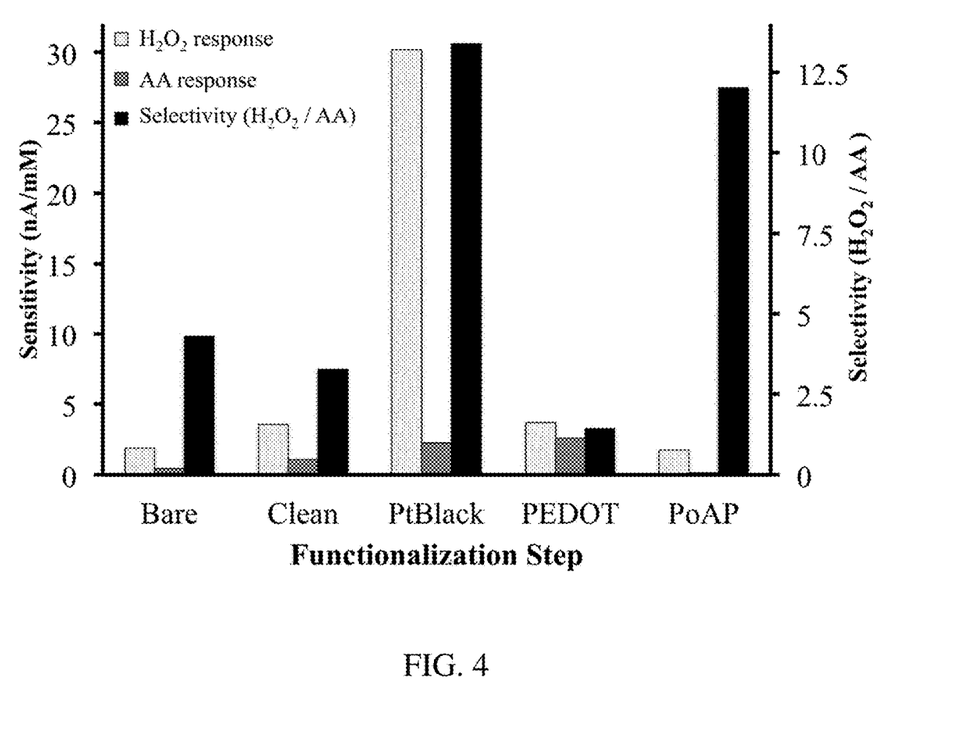
FIG. 4 is a graph showing directed electrodeposition of three consecutive functionalization layers results in enhanced selectivity for $H_2O_2$ over Ascorbic Acid (AA). The three layer design allows for independent control of electroactive surface area enhancement (Pt Black), enzyme doping (PEDOT) and interference rejection (PoAP).

The use of three distinct functionalization layers allowed independent control of three key sensor metrics namely, electroactive surface area, transducer doping (discussed below) and interference rejection. FIG. 4 outlines the changes in $H_2O_2$ sensitivity and selectivity of the microwire after each functionalization step. Electrode cleaning in sulfuric acid and electrodeposition of platinum black onto the exposed tip led to over a one-fold increase in electroactive surface area, evidenced by increased $H_2O_2$ sensitivity and enhanced selectivity over ascorbic acid. The second, PEDOT based enzyme entrapment layer showed improved exclusion of both $H_2O_2$ and AA, but reduced $H_2O_2$ sensitivity. The use of a final, enzyme doped PoAP layer served to restore selectivity owing to the unique permselective properties of this polymer at neutral pH. Together, the two electrodeposited polymer layers allow controlled transducer doping and reduced interference from anionic species such as ascorbic acid.

The individual parameters for each functionalization layer were first optimized for the detection of glucose using the model enzymatic transducer glucose oxidase. Square wave chronopotentiometry was used for platinum black deposition as it allowed easy control of total injected charge. The potential at the electrode was monitored during deposition to ensure repeatability of the final electroactive surface area (conductivity) of the modified tips. The two electroactive polymer layers were deposited one after another using multiple rounds of potential cycling in aqueous enzyme doped monomer solutions. Typical aqueous electrodeposition strategies for EDOT use negatively charged polymers such as PSS to improve monomer solubility and lower deposition potentials (0 to 1.2V) that rely on passive adsorption for enzyme loading into the growing polymer film. The polar aprotic solvent dimethyl sulfoxide (DMSO, 5% v/v) was used in this scheme to obtain a stable dispersion of EDOT monomer in aqueous enzyme solution without the use of additional negatively charged polymers such as PSS. The omission of PSS prevents competition between PSS and the negatively charged enzymatic transducer for incorporation into the growing polymer film. Further, the potential range for deposition was raised compared to previously reported methods, thereby enabling electrochemically aided adsorption of enzyme, permitting active transducer doping and tunable sensitivity to the analyte of interest. The final permselective PoAP layer was grown using previously described methods but at higher enzyme doping. The increased enzyme concentrations used in both polymer growth solutions were found to be necessary to achieve enhanced sensitivity in the micro-scale form factor.

Figure 5A:
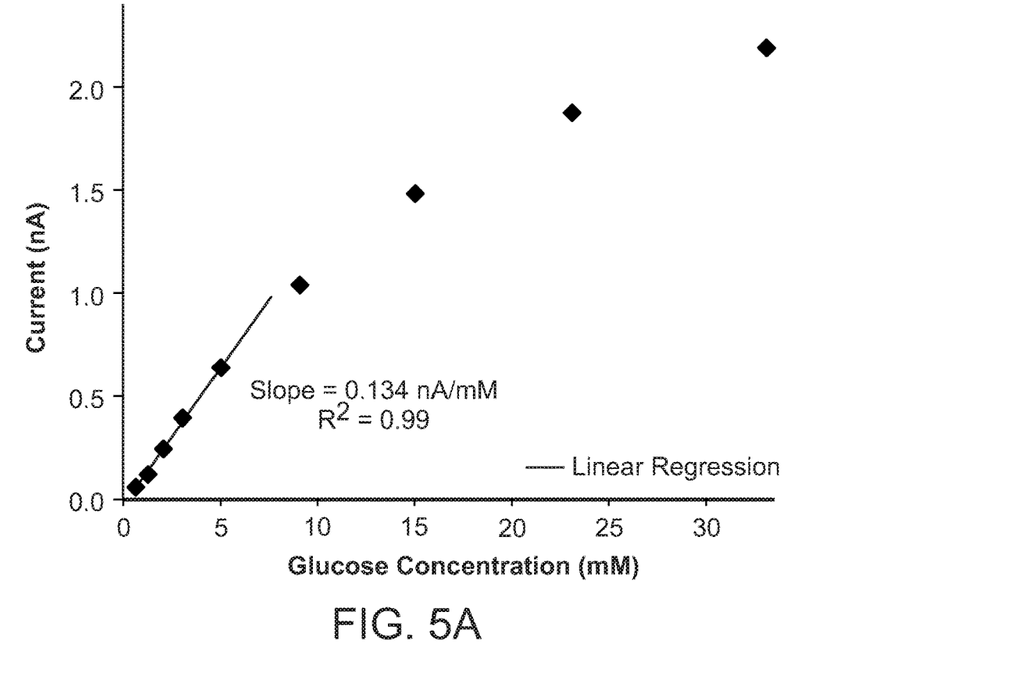
FIGS. 5A-B are graphs showing that glucose and lactate sensors show physiologically relevant linear calibration ranges. Representative calibration plots for glucose (5A) and lactate (5B) sensors using sequential analyte additions at a polarization potential of 0.5V. Sensors show a linear calibration range of $2\times10^{-5}$-$8\times10^{-3}$ M for Glucose and $4\times10^{-6}$-$2.5\times10^{-4}$ M for Lactate. Typical response times were 2-5 s.

The resulting glucose sensors were validated via calibration against known step additions of glucose at a detection potential of 0.5V. FIG. 5A shows the calibration plot for a representative glucose sensor with a linear calibration range of $2 \times 10^{-5}$–$8 \times 10^{-3}$ M. Typical response times were in the range of 2-5 seconds.

Figure 6A:
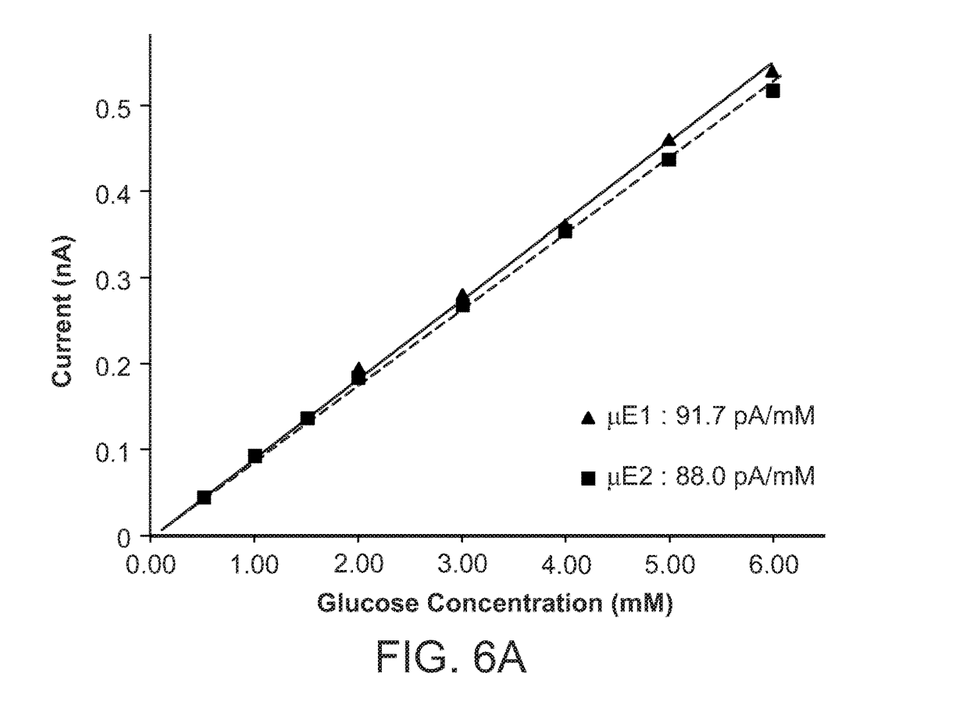
FIGS. 6A-C are graphs showing that fabricated sensors showed consistent and stable sensitivity to analyte. Sensors fabricated using the same functionalization solutions demonstrated similar sensitivities (6A). Sensor response was stable over one week of testing (6B, n=3) with no change in the linear sensing range (6C).
Figure 6B:
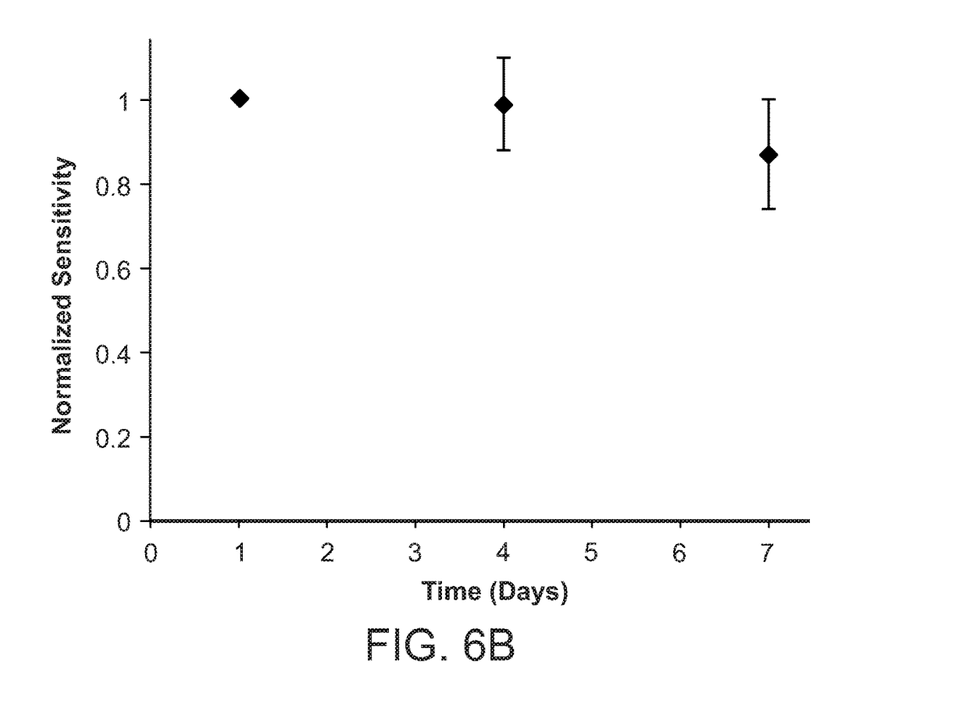
Figure 6C:
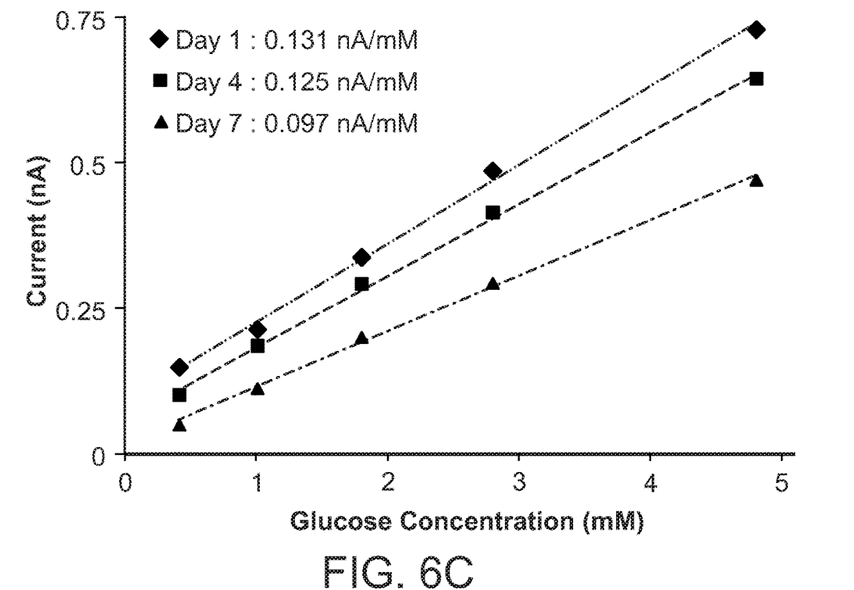

Another advantage of the scheme is the ability to produce consistent sensors with similar sensitivities when using the same functionalization solutions and electrochemical deposition parameters for the three layer. FIG. 6A shows the responses of two individually functionalized single wire micro-electrodes to the same concentration increments of glucose. Inter-sensor variability <5% can be easily achieved by monitoring electrode conductivity during Pt Black electrodeposition and total charge injected in each polymer deposition step of the scheme. Further, the stability of resulting sensors was tested by monitoring sensitivity of sensors over a period of one week (FIG. 6B). Sensor response decreased by <20% over one week of testing (n=3) when stored at 4° C. Further, the linearity and operating range of the sensors was maintained over the entire testing period (FIG. 6C).

Figure 5B:
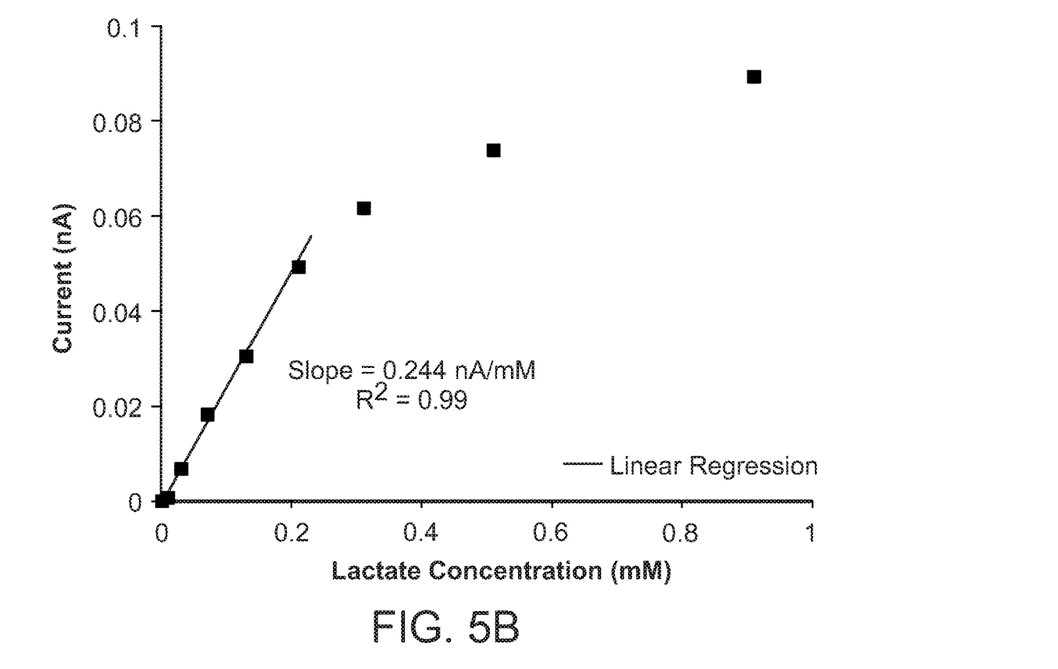

Finally, the functionalization steps and parameters optimized for glucose sensors were applied to fabricate lactate sensors by simply replacing the enzyme in the scheme with lactate oxidase. The resulting sensors showed linear calibration for lactate in the range $4 \times 10^{-6}$–$2.5 \times 10^{-4}$ M with similar response times at a detection potential of 0.5V (FIG. 5B).

An important requirement for multi-analyte sensing whether in multi-wire format or on chip is that the responses from individual analyte sensor sites (in this case current) are all within the measurable range of the potenstiostat or onboard circuitry. The ability to tune the sensitivity (current response of the sensor per unit change in analyte) of each specific site and do so in a repeatable fashion can help avoid complex measuring circuitry and maximize the signal to noise ratio of the system by matching the linear sensing range to the current measurement range. Most electroactive polymer based functionalization schemes reported to date rely on passive adsorption of the enzyme onto the electrode for incorporation into the growing polymer film. The only way to control enzyme doping in such schemes is by increasing the concentration in the functionalization solution. Moreover, as most of the enzyme is typically incorporated in the first deposition cycle, the upper limit for sensitivity is defined by the size of the electrode surface. This limits the scalability of such schemes and makes it difficult to achieve tunable sensitivity in microscale form factors.

Figure 7A:
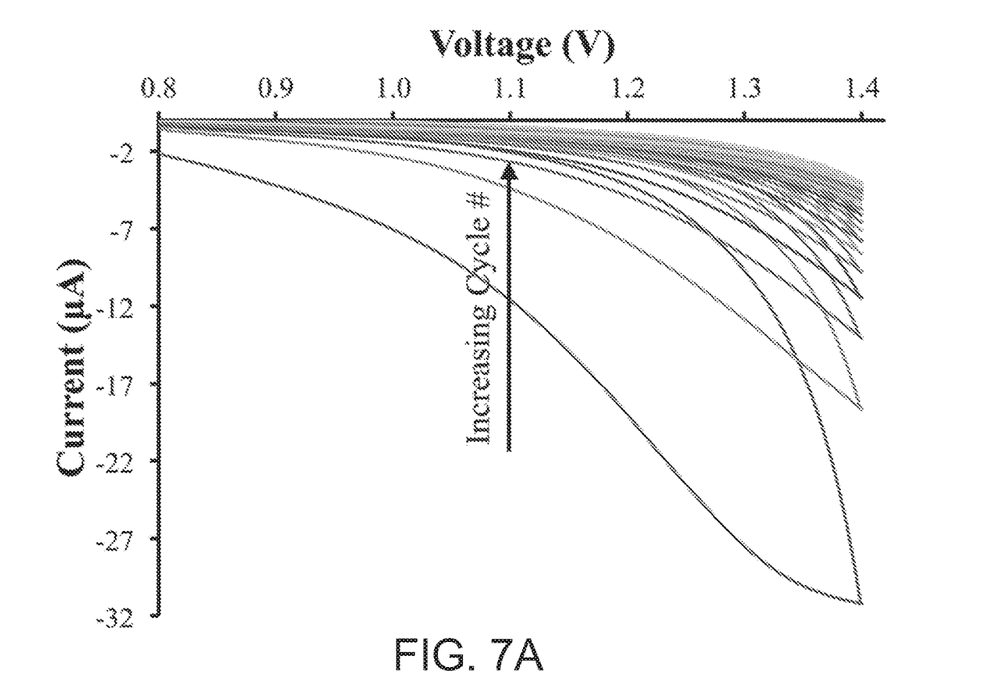
Figure 7B:
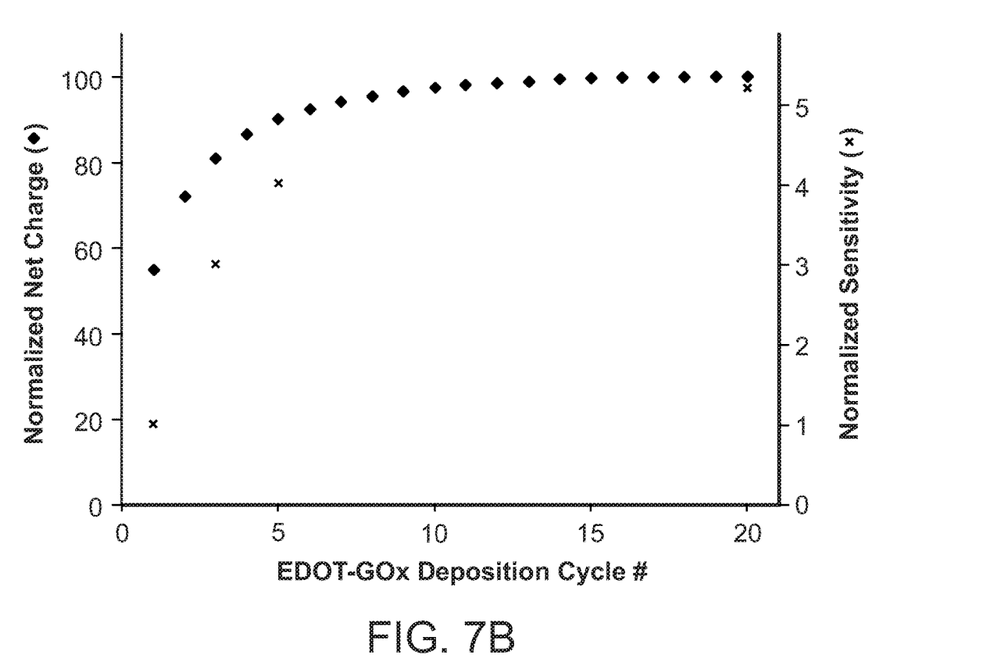

Methods of the invention provide for tunable enzyme doping in this scheme because of several important design decisions pertaining to the electrodeposition of the PEDOT transducer doping layer as discussed earlier. Selection of appropriate electrolyte pH, elimination of competing negative counter ions such as PSS and use of higher electrodeposition potentials allowed for active doping of negatively charged enzymatic transducer. Tunable sensitivity to the analyte of interest is easily achieved by varying the number of cycles of EDOT film growth. FIG. 7B. shows a 5 fold increase in sensitivity between the 1st and 20th cycle of electrodeposition for a fixed concentration of enzyme. Further increases in sensitivity are limited by the decrease in the conductivity of the film, and progressive reduction in charge injected per deposition cycle (FIG. 7A) with increasing cycle number. Higher electro-deposition potentials have been previously shown to produce films with reduced conductivity because of the oxidation of the resulting polymer at these potentials.

Figure 7C:
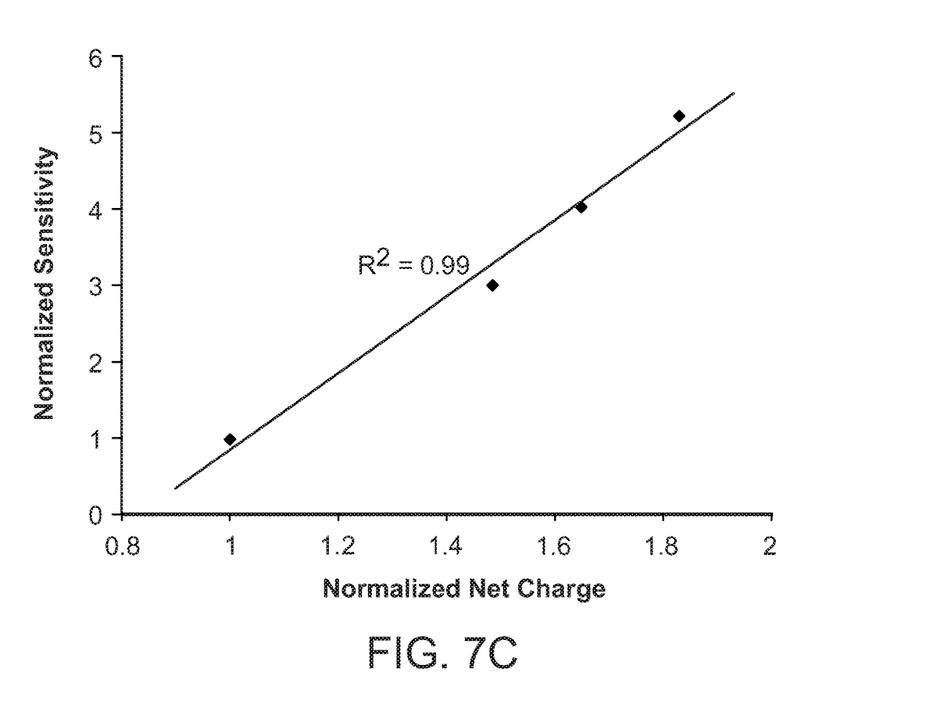

Plotting the tuning curve for the same sensor shows that analyte sensitivity is linearly correlated to the net charge injected (an indicator of the polymer film growth; FIG. 7C). This result is a significant improvement over existing methods as charge injection is easily monitored during deposition and provides a simple metric to precisely control the level of enzyme doping and hence sensitivity of the resulting sensor.

As discussed above, the use of electrodeposition allows directed modification of specific sensing surfaces and can be used for multiplexed or multi-analyte sensing. The deposition methods for this design were expressly selected to enable site-specific functionalization of multiple enzymes in closely spaced electrodes.

Once the individual parameters for glucose and lactate sensor functionalization were optimized using single microwire electrodes they were used to demonstrate applicability of the scheme for high resolution multi-analyte sensing using commercial stereoelectrodes. Both electrodes were immersed simultaneously in functionalization solutions for both analytes. Tunable sensitivity for glucose or lactate was achieved at the electrode of interest by appropriate selection of enzyme concentration and number of deposition cycles. Use of a potential of 0V to −100 mV prevented non-specific functionalization and fouling at the opposite electrode.

Figure 8A:
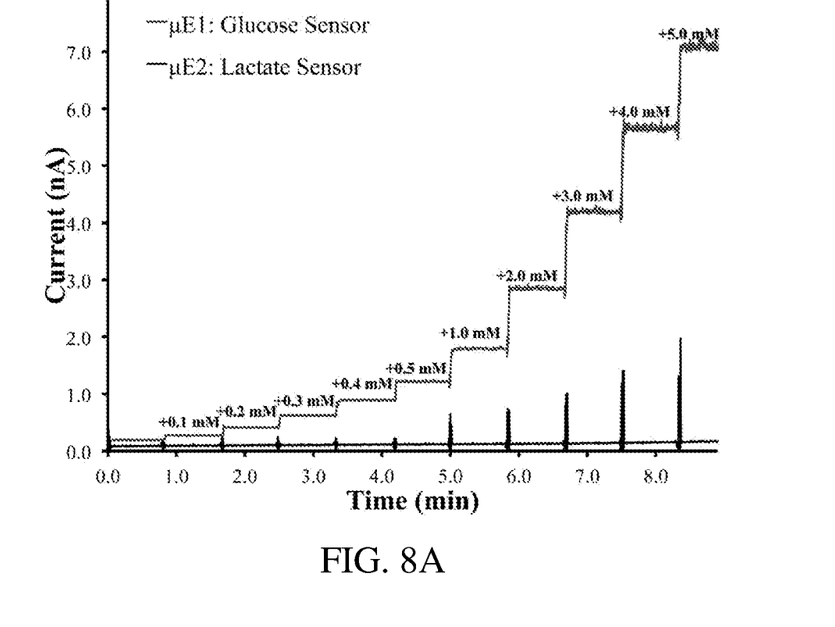
FIGS. 8A-B are graphs showing that stereo-electrode sensors show linear sensing ranges similar to single-electrode counterparts and demonstrate multi-analyte capability of functionalization scheme. One microelectrode each of the stereo-electrode pair were functionalized with glucose oxidase (µE1) and lactate oxidase (µE2) for simultaneous glucose and lactate sensing. Shown are concurrently recorded responses of the both microelectrodes of the stereo-electrode pair to additions of glucose (8A) and lactate (8B) at a biasing potential of 0.5 V under rapid stirring.
Figure 8B:
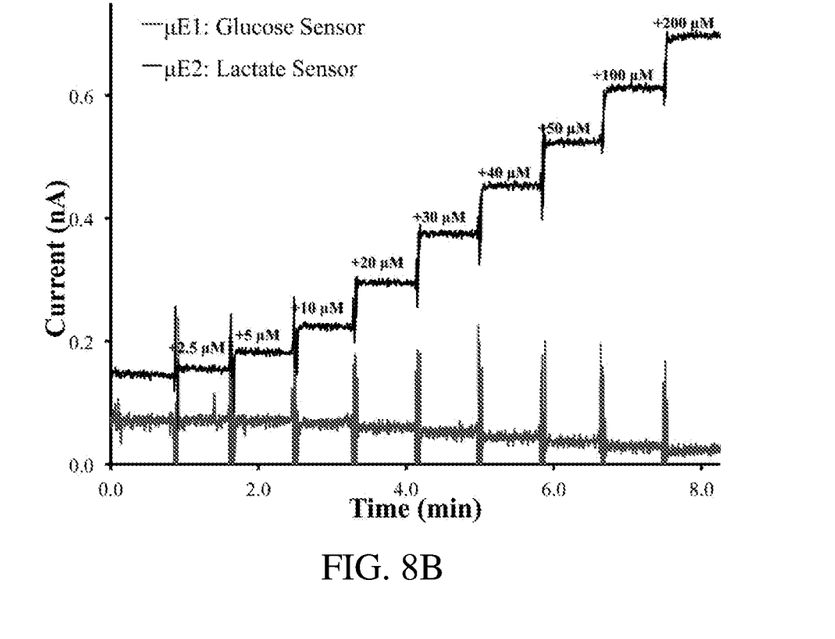

The resulting dual-analyte stereo-electrode was validated in bi-potentiostat mode with both wires simultaneously biased at 0.5V against a common reference electrode. The current responses of both electrodes (µE1: glucose sensor, µE2: lactate sensor) were recorded during standard glucose (FIG. 8A) and lactate (FIG. 8B) calibration experiments. Sensor linear ranges and response times showed agreement with those of single wire sensors, showing that the additional two steps of functionalization and the use of a potential between 0 mV and −100 mV was not detrimental to sensor response.

Figure 9:
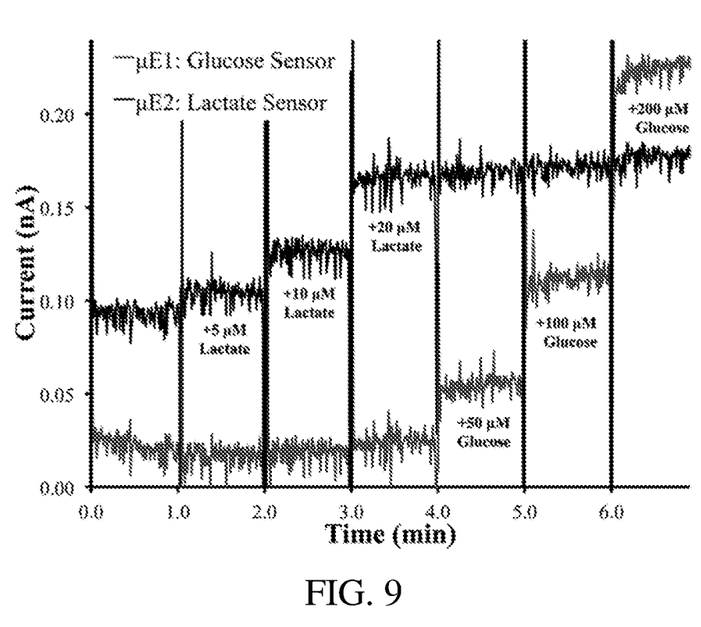

Finally, the responses of the same dual sensor were recorded for three step additions each of lactate and glucose as shown in FIG. 9. Both sensors showed strong selectivity for their respective analytes and no response to concentration changes of the opposite analyte. Taken together, these two experiments demonstrate the spatial control afforded by this scheme and demonstrate the applicability of the same to multi-analyte sensing.

The simple three-layer functionalization scheme described here allows for spatially directed functionalization of sensing surfaces for enzyme-based amperometric sensing. Each functionalization layer is shown to serve an important role in defining the characteristics of the final sensor. The initial platinum black layer greatly enhances the effective surface area of the electrode surface while maintaining a small sensing footprint. The second electrodeposited PEDOT layer is shown to be capable of active transducer doping, allowing the sensitivity to be easily tuned with no change in linear sensing range. This method is an improvement over previously reported sensing schemes based on electroactive polymer film growth that rely primarily on passive adsorption for transducer doping and are hence not easily tunable. The final electrodeposited PoAP layer provides a fold increase in selectivity for $H_2O_2$ over common interferents such as ascorbic acid. The combination of these three functionalization layers affords consistent, spatially controlled doping of transducers for enzyme-based amperometric sensors for high-resolution single/multi-analyte physiological sensing.

Multi-analyte capability of this design is demonstrated using custom stereo-electrodes that are functionalized with enzymes for simultaneous glucose and lactate sensing. Both sensing electrodes are addressed simultaneously and show physiologically relevant linear sensing ranges for their analytes, negligible crosstalk, fast response times and decreased interference. These results validate the applicability of the functionalization scheme for multi-analyte sensing and pave the way for simultaneous real-time sensing of multiple analytes in various physiological settings.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

A three-layer functionalization scheme was developed that employs electroactive polymer nanocomposites to achieve tunable, site-directed functionalization for enzyme-based biosensors. Nanostructured platinum [Pt Black], enzyme-doped conductive polymer poly(3,4-ethylenedioxythiophene) [PEDOT] and non-conductive polymer poly(o-aminophenol) [PoAP] were electrodeposited as consecutive layers to achieve increased electroactive surface area, fine control over location and quantity of enzyme, and reduced interference, respectively. Optimization of deposition parameters allowed unprecedented control over enzyme doping and consequently analyte sensitivity of resulting biosensors. The design was first validated by controlled functionalization of a 1-3 µm tip size microelectrodes for glucose and lactate sensing. Resulting sensors showed tunable sensitivity, reduced interference, physiologically relevant linear sensing ranges, short response times and were stable over the period of testing. Finally, multi-analyte capability of the scheme was demonstrated via simultaneous glucose and lactate sensing using custom stereo-electrodes with 1-3 µm sensing areas and 75 µm tip separation. Use of an exclusively electrode driven, electrodeposition based functionalization scheme enabled 5× sensitivity tuning, spatially controlled transducer doping unattainable with conventional dip, drop or spin coating based methods, and allowed the extension of the scheme to multi-analyte sensing using multi-electrode systems and lab-on-chip platforms. The following are exemplary embodiments of the invention.

Example 1: Reagents

Phosphate buffered saline (PBS 0.01 M pH 7.4), chloroplatinic acid solution (8% wt/wt), lead (II) acetate trihydrate (99%), 3,4-Ethylenedioxythiophene (EDOT, 97%, stored at 4° C.), H2O2 (30% (w/w) in H2O, stored at 4° C.), D-glucose (99.5%, BioXtra), dimethyl sulfoxide (99.7%, HPLC grade), sodium acetate buffer solution (3M, pH 5.2), sodium ascorbate and sulfuric acid (98%) were purchased from Sigma-Aldrich (St. Louis, Mo.). Glucose oxidase (Aspergillus niger, lyophilized powder, 220 units/mg, stored at 20° C.) and Lactate oxidase (Aerococcus viridians lyophilized powder, 20 units/mg, stored at 20° C.) were obtained from Sekisui Diagnostics (Kent, UK). 2-aminophenol (o-AP, 99%) and sodium lactate (60% w/w) were purchased from Alfa Aesar (Ward Hill, Mass.). All buffers and functionalization solutions, if not specified, were prepared in deionized water (DI) of resistivity 18.2 MΩ cm (Ultrapure water).

Example 2: Apparatus and Electrodes

Platinum/Iridium (Pt/Ir) microelectrodes (P120033.0A10, Microprobes Inc., Gaithersburg, Md.) with 256 µm diameter shaft, 3 µm parylene C insulation, 1-3 µm exposed tip diameter and, 3.0 MΩ impedance were used for the design and characterization of the three-layer functionalization scheme. PEDOT doping tests were conducted using 1.6 mm diameter Pt disk electrodes (MF-2013, BASi Inc., West Lafayette, Ind.). Custom fabricated Pt/Ir stereotrodes (Microprobes Inc., Gaithersburg, Md.) with 75 µm diameter shaft, 3 µm parylene C insulation, 1-3 µm exposed tip diameter, 75 µm tip separation and, 3.0 MΩ impedance were used to demonstrate spatial control and multi-analyte capability of the functionalization scheme.

Figure 2:
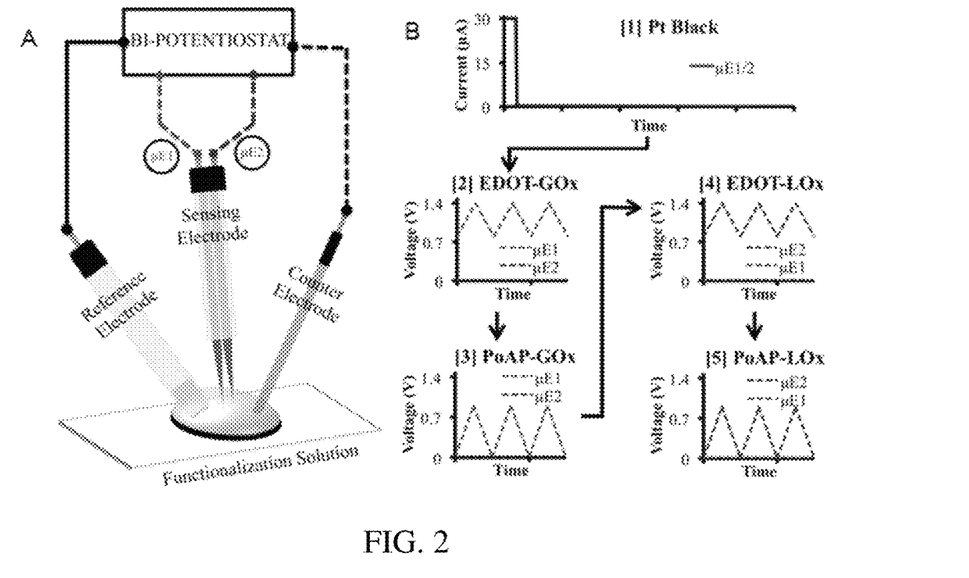

All functionalization steps and sensor characterization experiments unless specified, were performed in a standard three-electrode setup using a saturated silver/silver chloride reference electrode (BASi Inc., West Lafayette, Ind.) and a bare platinum wire counter electrode (0.5 mm dia, Alfa Aesar, Ward Hill Mass.). A custom functionalization setup was used to minimize functionalization solution volumes to 200 µL and optimize reagent utilization (FIG. 2A).

Example 3: Electrode Pretreatment, Cleaning and Storage

All microwire electrode tips were washed by sonication in Ultrapure water and dried in a stream of nitrogen gas before modification. The electrodes were then immersed in a 1M sulfuric acid solution and the potential cycled between 0.2 and 1.2 V vs. Ag/AgCl/KCl (sat'd) at 0.1V s−1 until a steady-state cyclic voltammogram was obtained. Prior to this electrochemical pretreatment, the 1.6 mm disk electrodes used to characterize enzyme doping were first polished with alumina slurries (1 µm/0.3 µm/0.05 µm particles)

and then cleaned in Piranha solution to remove organic contaminants between differing functionalization cycles. Following this, all electrodes were again rinsed with liberal amounts of water before further processing. Fabricated sensors were rinsed in PBS and stored dry at 4° C. when not in use. Sensors were also rinsed briefly in PBS before and after all characterization experiments.

Example 4: Platinum Black Deposition

Prior to electrochemical enzyme immobilization, an initial layer of amorphous platinum black (Pt Black) was grown onto the exposed tip of microwire electrodes to increase effective surface area while maintaining small sensing footprint. Electrodes were subjected to pulsed current injection (square wave, 10 ms ON, 500 ms OFF) in a standard three-electrode setup while immersed in a platinizing solution composed of 17.5 mM Hexachloroplatinic acid and 0.03 mM Lead Acetate. An initial current train of amplitude 10 µA (25 cycles) was used to prime the electrode and initiate Pt Black deposition followed by a second train of amplitude 30 µA (100 cycles). The electrodes were then rinsed in ultrapure water and dried in a convection oven at 80° C. for 20 minutes.

Example 5: Enzyme Immobilization

Enzyme immobilization on electrode surfaces was achieved through electrochemical growth of PEDOT films by cyclic voltammetry (potential range 0.8V/1.4V vs. Ag/AgCl/KCl (sat'd) at 50 mV s−1, 1-20 cycles) using a 5 mM EDOT solution containing 2500 U ml−1 of either glucose or lactate oxidase in Ultrapure water. EDOT was first solubilized in DMSO to make a 50 mM stock solution, then diluted to 10 mM using incremental additions of water and finally vortexed for 20 minutes with an equal volume of the enzyme stock solution (5000 U ml−1) to achieve desired monomer and enzyme concentrations. All electrodes were rinsed in ultrapure water and air-dried prior to further processing.

Example 6: Permselective Poly(o-aminophenol) Layer

Permselectivity for interferents such as ascorbic acid was achieved using a final functionalization layer of poly(o-aminophenol) (PoAP) doped again with the enzyme of interest. PoAP films were electrochemically deposited via cyclic voltammetry (potential range 0V/0.9 V vs. Ag/AgCl/KCl (sat'd) at 50 mV s−1, 15 cycles) using a 5 mM o-AP solution containing 2500 U ml−1 enzyme in 0.05 M acetate buffer (pH 5.6). The monomer o-AP was first solubilized in 0.1 M acetate buffer via sonication to make a 10 mM stock solution that was then vortexed for 20 minutes with an equal volume of the enzyme stock solution (5000 U ml−1) to achieve desired monomer and enzyme concentrations. Fully functionalized electrodes were rinsed in PBS and air-dried prior to storage at 4° C.

Example 7: Dual-Electrode Functionalization

All stereoelectrode functionalization steps were performed by immersing both electrode tips in functionalization solutions simultaneously. The first two functionalization steps (i.e pretreatment and Pt Black) deposition were implemented on both microelectrode tips in sequence using the three electrode setup and functionalization solutions described previously. Enzyme biofunctionalization and permselective layer deposition were achieved using EDOT and o-AP solutions doped with glucose oxidase and lactate oxidase for electrodes 1 and 2 respectively. A total of four consecutive steps were used; both enzymatic bio-functionalizations were completed first, followed by growth of permselective layers. Appropriately doped PEDOT and PoAP layers were spatially confined to their respective electrodes via potential cycling at the electrode of interest as described earlier. In each case, the opposing electrode was held at a constant potential of 0 V to prevent non-specific adsorption of the enzymatic transducer or oxidized monomer onto the tip. As an added precaution, the entire electrode shank was rinsed in ultrapure water after each deposition step and in PBS after completion of all four functionalization steps.

Example 8: Electrochemical Measurements

Amperometric sensitivity of both micro and macro electrode based sensors was determined by measuring $H_2O_2$ oxidation current at a constant working potential of 0.5V upon sequential additions of requisite analyte stock solution to a known volume of PBS. Following each addition, measured current signal was allowed to reach steady state for at least 10 seconds. Plots of average current versus analyte concentration were used to represent sensor response, and linear regression was used to estimate sensitivity, and linear sensing range (R2>0.98) Limit of detection for each sensor was computed using the 3σ (i.e., 99% confidence) method. Sensor tunability was determined by measuring glucose response after varying number of PEDOT functionalization cycles using 1.6 mm diameter Pt disk electrodes. Sensor sensitivity was normalized to account for variations in available electroactive surface area after multiple functionalization and cleaning steps.

Example 9: Controlling Biomolecule Deposition in Space

The above described methods allow for controlling biomolecule deposition in space and are able to tune a level of molecule-doping based on number of cycles of polymer growth. That enables biomaterial deposition on any conductive surface irrespective of shape and organization, as well as 3D patterning of biomolecules. Once patterned, the biomolecules can be used to detect analytes using electrical methods or other available detection modalities including but not limited to phosphorescence, fluorescence, SPR and Mass Spectrometry.

What is claimed is:
1. A method for detecting one or more target biological molecules in a sample, the method comprising:
    providing a multi-analyte sensor that comprises a plurality of sensing electrodes, each sensing electrode comprising at least one electrically conductive material and being functionalized with a different enzyme composition from other sensing electrodes of the plurality, wherein at least two of the plurality of sensing electrodes are spaced apart at a microscale level prior to and after functionalization and there is negligible cross-talk between the plurality of sensing electrodes, wherein each sensing electrode comprises: a first layer comprising a first electrically conductive material, a second layer comprising a second electrically conductive material, and a third layer comprising a third electrically conductive material; wherein conductivity of the third electrically conductive material is pH dependent, and wherein the first layer is platinum black, the second electrically conductive biocompatible material is poly (3,4-ethylenedioxythiophene), and the third electrically conductive material is poly(o-aminophenol);

contacting a sample to the multi-analyte sensor; and detecting one or more target biological molecules from the sample, wherein each of the one or more target biological molecules is detected on a different sensing electrode of the plurality of sensing electrodes.

2. The method of claim 1, wherein for each sensing electrode respectively, each of the different enzymes is present in the second and third layers.

3. The method of claim 1, wherein the multi-analyte sensor further comprises a control unit that comprises first and second electrodes, wherein the first electrode is a reference electrode and the second electrode is a counter electrode.

4. The method of claim 1, wherein a first enzyme is glucose oxidase.

5. The method of claim 4, wherein a first of the one or more target biological molecules is glucose.

6. The method of claim 5, wherein a second enzyme is lactate oxidase.

7. The method of claim 6, wherein a second of the one or more target biological molecules is lactate.

8. The method of claim 1, wherein the one or more target biological molecules are detected simultaneously.

9. The method of claim 1, wherein the sensing electrodes align with each other.

10. The method of claim 1, wherein the sensing electrodes are orthogonal to each other.

11. A method for detecting one or more target biological molecules in a sample, the method comprising:

providing a microchip that comprises a plurality of sensing electrodes, each sensing electrode comprising at least one electrically conductive material and being functionalized with a different enzyme composition from other sensing electrodes of the plurality, wherein at least two of the plurality of sensing electrodes are spaced apart at a microscale level prior to and after functionalization and there is negligible cross-talk between the plurality of sensing electrodes, wherein each sensing electrode comprises: a first layer comprising a first electrically conductive material, a second layer comprising a second electrically conductive material, and a third layer comprising a third electrically conductive material; wherein conductivity of the third electrically conductive material is pH dependent, and wherein the first layer is platinum black, the second electrically conductive biocompatible material is poly (3,4-ethylenedioxythiophene), and the third electrically conductive material is poly(o-aminophenol);

contacting a sample to the microchip; and detecting one or more target biological molecules from the sample, wherein each of the one or more target biological molecules is detected on a different sensing electrode of the plurality of sensing electrodes.

12. The method of claim 11, wherein for each sensing electrode respectively, each of the different enzymes is present in the second and third layers.

13. The method of claim 11, wherein the microchip further comprises a control unit that comprises first and second electrodes, wherein the first electrode is a reference electrode and the second electrode is a counter electrode.

14. The method of claim 11, wherein a first enzyme is glucose oxidase.

15. The method of claim 14, wherein a first of the one or more target biological molecules is glucose.

16. The method of claim 15, wherein a second enzyme is lactate oxidase.

17. The method of claim 16, wherein a second of the one or more target biological molecules is lactate.

18. The method of claim 11, wherein the one or more target biological molecules are detected simultaneously.

19. The method of claim 11, wherein the sensing electrodes align with each other.

20. The method of claim 11, wherein the sensing electrodes are orthogonal to each other.

* * * * *